United States Patent
Smith

(10) Patent No.: US 6,662,660 B2
(45) Date of Patent: Dec. 16, 2003

(54) APPARATUS FOR TESTING ARAMID FIBER ELEVATOR CABLES

(75) Inventor: Rory Smith, Germantown, TN (US)

(73) Assignee: Thyssen Elevator Capital Corp., Whittier, CA (US)

(*) Notice: Subject to any disclaimer, the term of this patent is extended or adjusted under 35 U.S.C. 154(b) by 33 days.

(21) Appl. No.: 09/953,689

(22) Filed: Sep. 17, 2001

(65) Prior Publication Data

US 2003/0052695 A1 Mar. 20, 2003

(51) Int. Cl.[7] .......................... G01H 5/00; G01N 29/00; G01R 31/08
(52) U.S. Cl. .............. 73/597; 73/602; 324/535
(58) Field of Search ................... 324/535, 539, 324/542; 73/597, 598, 602, 643, 620, 632; 367/127, 3

(56) References Cited

U.S. PATENT DOCUMENTS

| | | | |
|---|---|---|---|
| 4,295,212 A | * 10/1981 | Swenson | 368/20 |
| 4,445,593 A | * 5/1984 | Coleman et al. | 187/413 |
| 4,622,853 A | 11/1986 | Leugers | 73/597 |
| 4,947,851 A | 8/1990 | Sarvazyan et al. | 128/660.02 |
| 4,979,125 A | * 12/1990 | Kwun et al. | 702/35 |
| 5,456,113 A | 10/1995 | Kwun et al. | 73/587 |
| 5,834,942 A | 11/1998 | De Angelis | 324/522 |
| 6,236,218 B1 | * 5/2001 | Johansson et al. | 324/536 |
| 6,450,036 B1 | * 9/2002 | Ashida et al. | 73/584 |

OTHER PUBLICATIONS

M. Ferreira, T.M. Lam, V. Koncar, Y. Delvael, "Non-destructive testing of Polyaramide Cables by Longitudinal Wave Propagation: Study of the Dynamic Modulus", Polymer Science Engineering, Jul. 2000, vol. 40, No. 7, pp. 1628–1634.

* cited by examiner

Primary Examiner—Anjan K. Deb
(74) Attorney, Agent, or Firm—White & Case LLP

(57) ABSTRACT

The invention concerns an apparatus for inspecting and calculating the residual strength of an aramid fiber cable driving an elevator to determine when such cable is in need of replacement. The apparatus includes a transmitter for introducing an acoustic wave that will travel along the aramid fiber cable and a receiver for receiving the acoustic wave after its has traversed a designated section of the cable. The transmitter and receiver provide signals indicating the times the wave was sent by the transmitter and thereafter received by the receiver. From these signals, a program in the system calculates the wave velocity and the modulus, and the residual strength of the aramid cable.

12 Claims, 1 Drawing Sheet

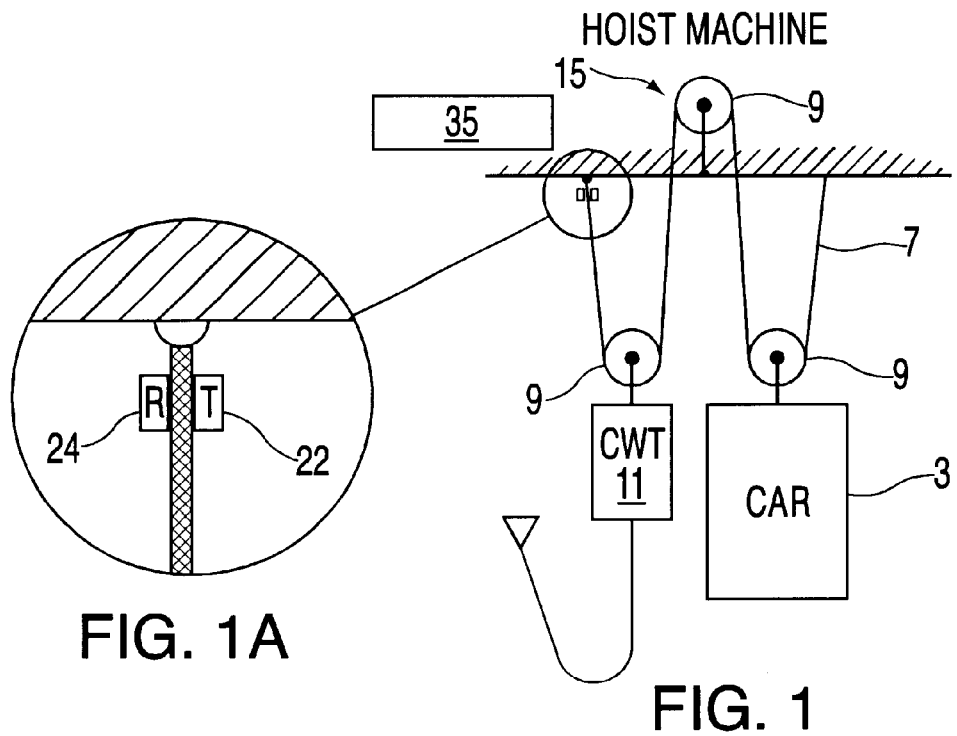
FIG. 1
FIG. 1A
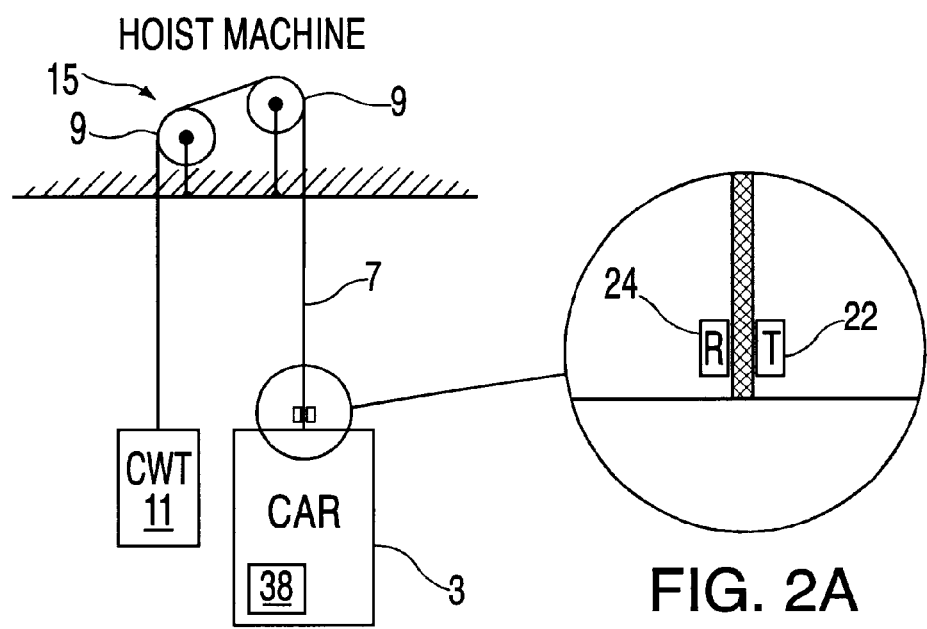
FIG. 2
FIG. 2A

APPARATUS FOR TESTING ARAMID FIBER ELEVATOR CABLES

FIELD OF THE INVENTION

The present invention relates to elevator systems. More particularly, the invention relates to an apparatus for testing aramid fiber cables used in elevator systems in order to determine when such cables are in disrepair and in need of replacement.

BACKGROUND OF THE INVENTION

Traditional steel elevator cables can easily be visually inspected for wear. The individual wires will break and these breaks can be easily observed. Aramid fiber elevator cables are covered with a protective sheathing that makes visual inspection impossible. If the ropes were not sheathed, it would still be difficult to determine the proper time to replace the ropes because the appearance of the fibers is almost identical whether the fibers are new or in need of replacement.

U.S. Pat. No. 5,834,942, to De Angelis, issued Nov. 10, 1998, discloses an apparatus for determining when a synthetic fiber cable (such as an aramid cable) for an elevator is ready for replacement. The apparatus includes a voltage detection device for detecting a voltage in at least one carbon fiber of the synthetic fiber cable and at least one threshold device for determining when the detected voltage exceeds a predetermined voltage threshold. The detected voltage is dependent upon the integrity of the portion of the synthetic cable (in particular the carbon fibers therein). Exceeding the predetermined voltage threshold is indicative of a failure of the portion of the cable. The prior art device has resorted to placing conductive fibers within the cable so that the fibers can be monitored by electrical means. This apparatus, therefore, may not be suitable for synthetic cables that are not readily conductive.

Those skilled in the art of aramids have shown that the elastic properties of aramid materials can be determined from the measurement of wave propagation through the material. (See M. Ferreira et al., "Nondestructive Testing of Polyaramide Cables by Longitudinal Wave Propagation: Study of the Dynamic Modulus", Polymer Engineering and Science, Vol. 40, No.7, July 2000). In particular, it has been observed that polyaramide cables at different states of fatigue have their own speed of longitudinal propagation of acoustic waves. It has been observed that longitudinal waves travel through aramid fiber ropes in accordance with the following formula:

$$V^2 = \frac{E}{\rho} \quad \text{(Equation 1)}$$

where V=velocity of wave propagation, E=dynamic or sonic modulus, and ρ=density. Since tensile modulus and acoustic modulus both change at the same rate with fatigue it is possible to calculate tensile modulus from the observed values of wave propagation. Plotting E (modulus) against Fr (residual strength), it was found that E=f(Fr). In other words, a quantifiable relationship exists between modulus (determined from velocity) and residual strength.

A similar relationship between modulus and residual strength may be determined for aramid cables used in elevator systems. The relationship will vary based on the particular aramid material used in and the dimensions of the cable. Once the relationship is determined, it will be possible to extrapolate the residual strength from determinations of modulus. This has not heretofore been achieved for elevator systems.

Thus, it is an objective of the present invention to provide an apparatus for inspecting aramid fiber elevator cables and for calculating the residual strength of such cables to determine when they need replacement.

SUMMARY OF THE INVENTION

The present invention concerns an apparatus for inspecting and calculating the residual strength of an aramid fiber cable driving an elevator to determine when such cable is in need of replacement. The apparatus includes a transmitter for introducing an acoustic wave that will travel along the aramid fiber cable and a receiver for receiving the acoustic wave after its has traversed a designated section of the cable. The transmitter and receiver provide signals indicating the times the wave was sent by the transmitter and thereafter received by the receiver.

The invention provides a means for processing the first and second signals to calculate the residual strength of the cable. In particular, the invention provides an elevator control system connected to the transmitter and receiver. The control system has a program and associated algorithms that calculate the velocity of the wave based on the times of the first and second signals. The program then calculates the modulus of the cable, and in turn determines the residual strength of the cable. The determination of residual strength is based on a stored equation showing the residual strength as a function of the modulus. The stored equation will vary depending on the particular aramid cable being used in the system.

The transmitter and receiver may be disposed at different locations along the cable. However, in a preferred embodiment, the transmitter and receiver are disposed at the same location along the cable and are placed at a nominal distance from a sheave used in the elevator system. In this case, the velocity of the wave is calculated by measuring the time it takes for the wave to travel from the transmitter to the sheave and back to the receiver. In this embodiment, the transmitter and receiver may actually be contained within one unit.

The invention also concerns an elevator system incorporating an apparatus for inspecting the aramid cable used to drive the system. The elevator system typically comprises an elevator car, an aramid fiber cable connected to the car, a hoist machine having a drive motor for displacing the cable in order to move the car, one or more sheaves for guiding the displacement of the cable, and a counterweight coupled to cable for counter-balancing the weight of the car. The apparatus of the invention is incorporated into the system.

BRIEF DESCRIPTION OF THE FIGURES

FIG. 1 shows the invention embodied in a first elevator system.

FIG. 1A shows an enlarged view of the receiver and transmitter shown in FIG. 1.

FIG. 2 shows the invention embodied in a second elevator system.

FIG. 2A shows an enlarged view of the receiver and transmitter shown in FIG. 2.

DETAILED DESCRIPTION OF THE INVENTION

FIGS. 1 and 2 show the invention embodied in two different elevator systems. In these figures, like reference numerals represent like elements.

The system includes an elevator car 3 suspended by an aramid fiber cable 7. The aramid fiber cable rides over one or more sheaves 9 and is also coupled to a counterweight 11 in order to balance the system. A hoist machine 15, which includes one of the sheaves, drives the cable in either of two directions in order to raise and lower the elevator car 3.

The apparatus of the invention is incorporated into the systems as follows. Referring to enlarged views of FIGS. 1A and 2A, a transmitter 22 and a receiver 24, both of which are constructed from sonic sensors, are connected to the aramid fiber cable 7. Transmitter 22 contains components that can introduce an acoustic wave along the aramid fiber cable 7. Transmitter 22 introduces an acoustic wave that travels from the transmitter to the nearest sheave and is reflected from the sheave and returns to the 24 receiver. The transmitter 22 and receiver 24 generate signals that indicate the time the acoustic wave is initially introduced on the cable 7 and the time when the wave is thereafter received by the receiver 24.

A means for processing the first and second signals to calculate the residual strength of the cable is provided. In particular, the invention provides an elevator control system 35 that is connected to both the transmitter 22 and receiver 24. The control system 35 has a program containing the appropriate algorithms for calculating the velocity of the wave based on the first and second signals. The control system and program may be located in the machine room (as in FIG. 1). In addition, as shown in FIG. 2, the elevator car 3 may contain an interface 38 that receives signals from the transmitter and receiver and sends those signals to the control system. The program within the control system calculates the modulus of the cable, and in turn determines the residual strength of the cable from a stored equation representing residual strength as a function of modulus.

When the calculated residual strength drops below a predetermined threshold, the control system 35 will provide the appropriate notification that the aramid cable 7 needs replacement. If desired, the control system may also be programmed to shut down the system when the residual strength of the aramid cable 7 falls below the threshold. Values for the residual strength may be determined periodically and automatically stored in the control system's memory for use in predicting cable life. This is an important advantage because the cable may be tested and the residual strength determined without removing the elevator from service. In particular, the apparatus of the invention may continuously test the residual strength of the cable, and may do so by testing various portions of the cable while the elevator is in operation. By running tests on portions of the cables while the elevator car is located in various places within the system, the apparatus of the invention is ultimately able to test the entire length of the cable. One particular option in this regard, is for the apparatus to test various successive portions of the cable incrementally to provide an overall evaluation of the cable. Another option may be to test portions randomly.

What is claimed is:

1. An apparatus for inspecting and calculating the residual strength of an aramid fiber elevator suspension cable driving an elevator to determine when such cable is in need of replacement, the apparatus comprising:

a transmitter for introducing an acoustic wave within the aramid fiber cable and providing a first signal indicative of the time when the transmitter introduces the wave;

a receiver for receiving the acoustic wave traveling within the aramid fiber cable and providing a second signal indicative of the time when the receiver has received the wave; and a means for processing the first and second signals to calculate the residual strength of the cable.

2. An apparatus according to claim 1, wherein the means for processing the first and second signals comprises an elevator control system connected to the transmitter and receiver, the control system having a program and associated algorithms for processing the times of the first and second signals to calculate (i) the velocity of the wave, (ii) the modulus of the cable, and (iii) the residual strength of the cable.

3. An apparatus according to claim 2, wherein transmitter and receiver are disposed at different locations along the cable.

4. An apparatus according to claim 2, wherein transmitter and receiver are disposed at the same location along the cable.

5. An apparatus according to claim 2, wherein the transmitter and receiver comprise one unit.

6. An elevator system comprising:

a) an elevator car, an aramid fiber elevator suspension cable connected to the car, a drive motor for displacing the cable in order to move the car, one or more sheaves for guiding the displacement of the cable, and a counterweight coupled to cable for counter-balancing the weight of the car; and b) an apparatus for inspecting and calculating the residual strength of the aramid fiber cable to determine when such cable is in need of replacement, the apparatus comprising:

a transmitter for introducing an acoustic wave that will travel within the aramid fiber cable and providing a first signal indicative of the time when the transmitter sent the wave;

a receiver for receiving the acoustic wave traveling within the aramid fiber cable and providing a second signal indicative of the time when the receiver has received the wave traveling; and a means for processing the first and second signals to calculate the residual strength of the cable.

7. An elevator system according to claim 6, wherein the means for processing the first and second signals comprises an elevator control system connected to the transmitter and receiver, the control system having a program associated algorithms for calculating the velocity of the wave based on the first and second signals, the modulus of the cable, and the residual strength of the cable.

8. An elevator system according to claim 7, wherein transmitter and receiver are disposed at different locations along the cable.

9. An elevator system according to claim 7, wherein transmitter and receiver are disposed at the same location along the cable and the wave travels from the transmitter to the a sheave, is reflected in direction, and returns to the receiver.

10. An elevator system according to claim 7, wherein the transmitter and receiver comprise one unit.

11. An elevator system according to claim 7, wherein the apparatus is adapted to calculate the residual strength of various portions of the length of the aramid fiber cable while the elevator is in operation and at different locations within the system.

12. An elevator system according to claim 11, wherein the apparatus is adapted to calculate the residual strength of various portions of the aramid fiber cable incrementally to evaluate the entire cable.

* * * * *